US005793292A

United States Patent [19]

Ivey, Jr.

[11] Patent Number: 5,793,292
[45] Date of Patent: Aug. 11, 1998

[54] SYSTEM FOR INHIBITING USE OF A HAND-OPERATED MACHINE BY AN IMPAIRED INDIVIDUAL THROUGH DETECTION OF TOXINS IN THE INDIVIDUAL

[76] Inventor: Ellwood G. Ivey, Jr., P.O. Box 692, Savannah, Ga. 31402

[21] Appl. No.: 50,947

[22] Filed: Apr. 22, 1993

[51] Int. Cl.⁶ .......................... G08B 28/00; A61B 5/00
[52] U.S. Cl. .............................. 340/576; 128/632
[58] Field of Search ...................... 340/576; 180/272, 180/282; 123/198 DC, 198 DB; 128/632, 633, 635

[56] References Cited

U.S. PATENT DOCUMENTS

| | | | |
|---|---|---|---|
| 4,093,945 | 6/1978 | Collier et al. | 340/279 |
| 4,617,559 | 10/1986 | Slansky | 340/576 |
| 4,846,182 | 7/1989 | Fogt et al. | 128/632 |
| 4,957,108 | 9/1990 | Schoendorfer et al. | 128/632 |
| 4,960,467 | 10/1990 | Peck | 128/632 X |
| 5,050,604 | 9/1991 | Reshef et al. | 128/632 |
| 5,113,860 | 5/1992 | McQuinn | 128/632 |
| 5,220,919 | 6/1993 | Phillips et al. | 128/632 |
| 5,291,887 | 3/1994 | Stanley et al. | 128/632 X |

*Primary Examiner*—James J. Groody
*Assistant Examiner*—John W. Miller
*Attorney, Agent, or Firm*—Michael Drew

[57] ABSTRACT

A system for inhibiting use of a hand-operated machine by an impaired individual through detection of toxins in the individual has affixed to a portion of the machine which the operator regularly engages with his or her hands a porous membrane (5) impregnated with a substance (2) which reacts with a toxin by-product of an impairing substances such as alcohol, and another substance which causes the combined toxin and toxin-reacting substance to exhibit a color change. The system further contains a means (26) for detecting the color change in the membrane (5) and then causing a signal (14) to be displayed to the operator. Upon detection of the toxin-producing substance the system may also interrupt operation of the machine.

8 Claims, 2 Drawing Sheets

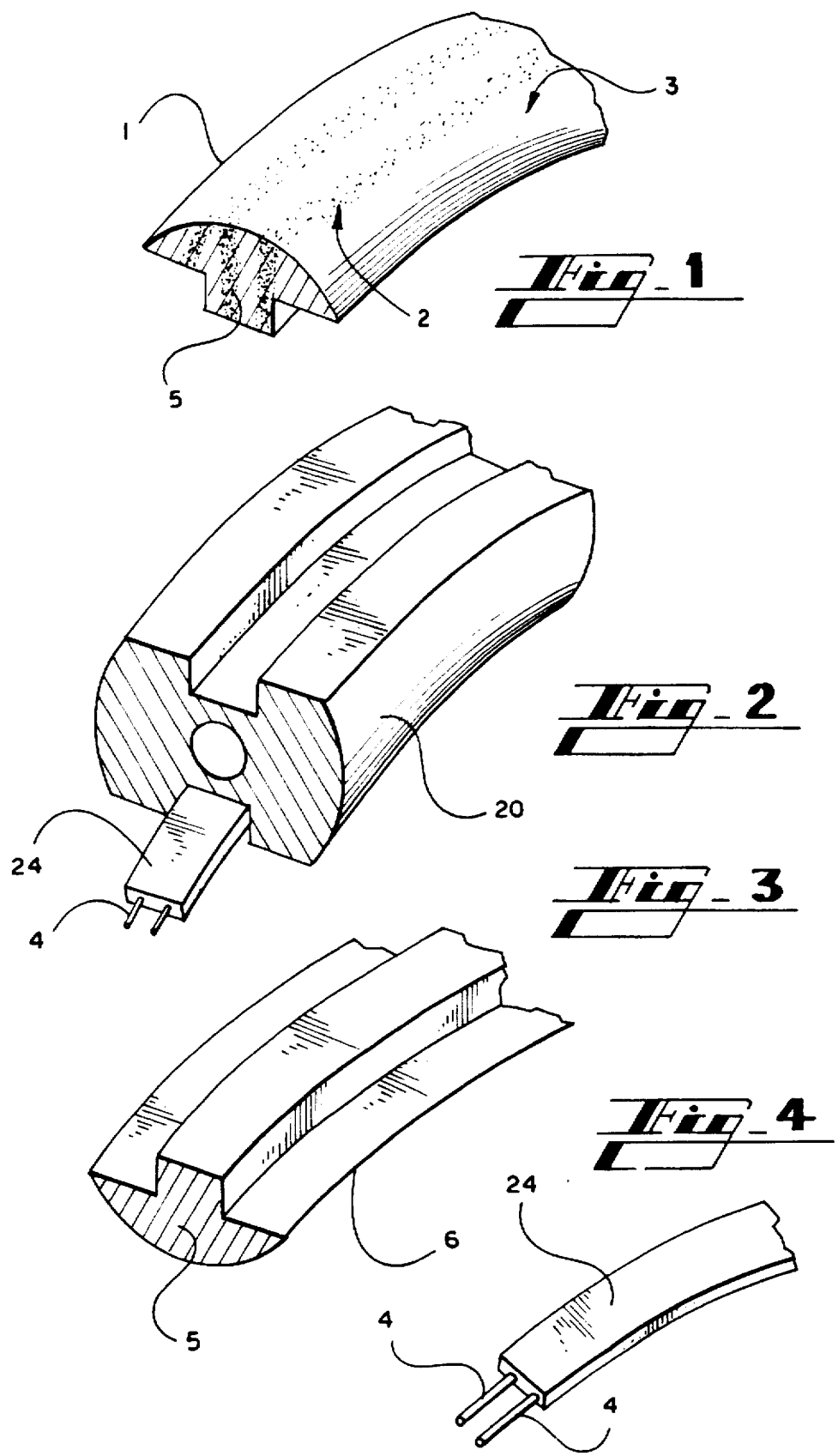

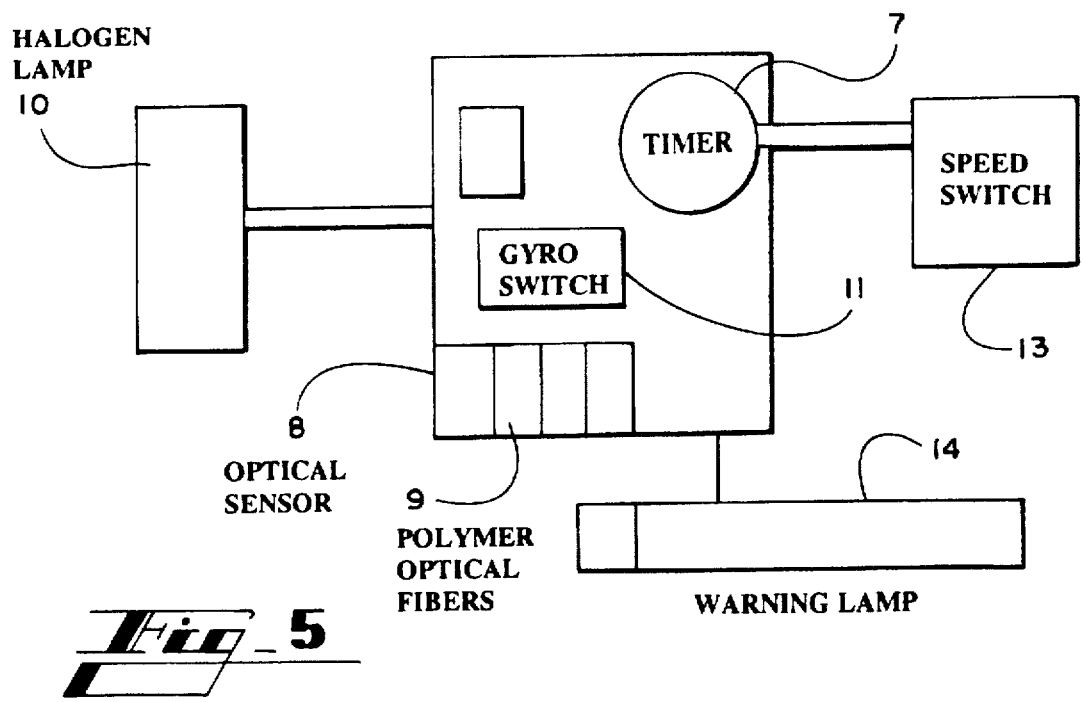
Fig_5
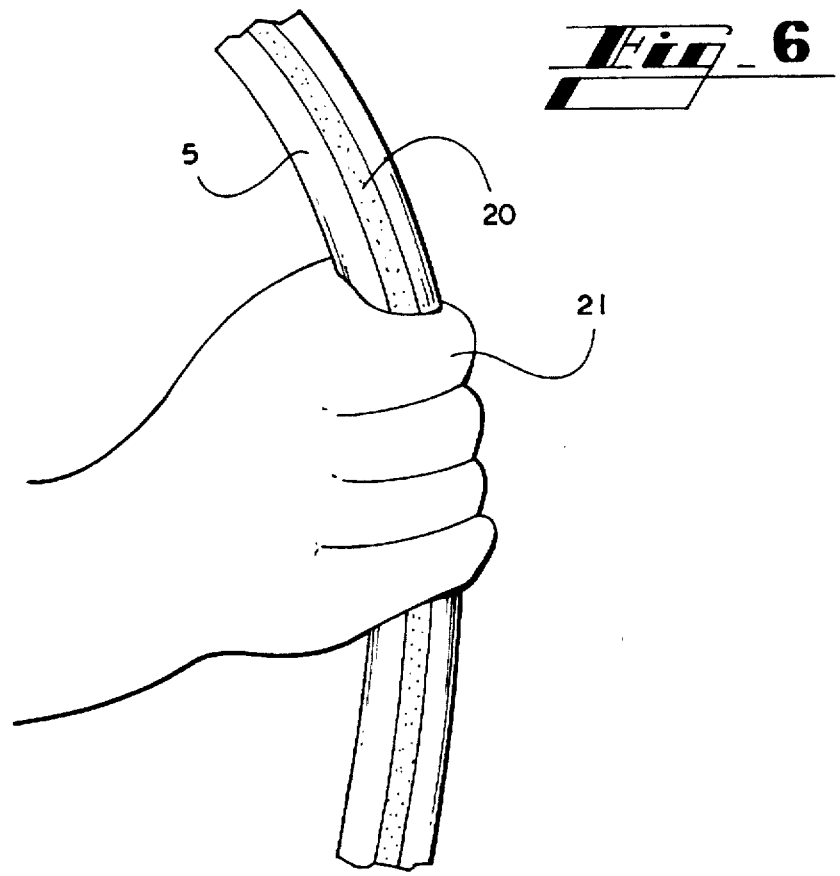
Fig_6

SYSTEM FOR INHIBITING USE OF A HAND-OPERATED MACHINE BY AN IMPAIRED INDIVIDUAL THROUGH DETECTION OF TOXINS IN THE INDIVIDUAL

The invention relates to a system integrated into a hand-operated machine, such as a motor vehicle, that non-invasively detects in an operator of the machine the presence of toxins associated with performance impairing substances, and subsequently inhibits operation of the machine upon the detection of the toxins.

BACKGROUND OF THE INVENTION

The presence and levels of certain types of toxins in the body of an individual is indicative of the presence of certain substances which are known to impair the performance capability of an individual. In industry, the level of certain toxins in the body of an employee is used to determine the employee's capability to perform on the job, whether the employee can perform the job safely and whether the employee is in compliance with company policy regarding use of substances (such as alcohol or cocaine) which produce the toxins. In the medical field the presence of toxins is known to aid in the determination of the origin of loss of motor function and life-threatening coma. In the legal field the level of certain toxins in the blood stream is used as an objective indicia of fitness to operate machinery or to drive an automobile or other vehicles. It is particularly important for law enforcement purposes to have a simple, fast, convenient, automated method of determining whether there are toxins in an individual's blood system related to substances such as alcohol and cocaine.

Known methods of integrating a toxin-testing device into a vehicle have been problematic. Examples of such problematic devices are disclosed in U.S. Pat. No. 4,093,945 and U.S. Pat. No. 3,886,540.

SUMMARY OF THE INVENTION

The present invention provides a passive, un-invasive means for detecting the presence of toxins related to performance-impairing substances in an operator of a hand-operated machine.

A system for inhibiting use of a hand-operated machine by an impaired individual through detection of toxins in the individual according to a preferred embodiment of the invention has affixed to a portion of the machine which the operator regularly engages with his or her hands a porous membrane impregnated with a substance which reacts with a toxin by-product of an impairing substance, such as alcohol, and another substance which causes the combined toxin and toxin-reacting substance to exhibit a color change. The system further contains a means for detecting the color change in the membrane and then causing a signal to be displayed to the operator. Upon detection of the toxin-producing substance the system may also interrupt operation of the machine.

Other advantages and objects of the present invention will be apparent from the following description, the accompanying drawings, and the appended claims.

BRIEF DESCRIPTION OF THE DRAWINGS

FIG. 1 is an isometric illustration of an impregnated membrane of a system for inhibiting use of a hand-operated machine by an impaired individual through detection of toxins in the individual according to a preferred embodiment of the invention.

FIG. 2 is an isometric illustration of a segment of a vehicle steering wheel suitable for receiving the membrane of the system of FIG. 1.

FIG. 3 is another isometric illustration of the membrane of FIG. 1 illustrating additional features of the system of FIG. 1.

FIG. 4 is an isometric illustration of the electrode and optical fiber assembly of the system elements shown in FIG. 2.

FIG. 5 is a block diagram of electrical components suitable for incorporation in the system of FIG. 1.

FIG. 6 is an isometric illustration of a steering wheel of a motor vehicle incorporating the membrane of FIG. 1 in a system for inhibiting use of a hand-operated machine by an impaired individual through detection of toxins in the individual according to a preferred embodiment of the invention in use as the steering wheel is grasped by the hands of an individual.

DETAILED DESCRIPTION OF THE PREFERRED EMBODIMENT

The present invention provides a system for utilizing the biological characteristics of humans to detect the presence of performance-impairing substances in an individual and subsequently limiting the individual's ability to continue operation a machine when the such substance is detected. The present invention utilizes the pharmacological characteristics of substances that may be found in an individual that are detectable at the skin. The invention's primary means of detecting the presence of a substance that may impair performance capabilities of an individual is based upon the characteristics of ethanol which is known to be produced in the body from consumption of impairing substances such as alcohol. The invention induces sweating, or perspiring, in the individual. The sweat will contain ethanol if present in the body. The sweat is caused to come in contact an ethanol assay which makes known the presence of ethanol. The assay substance also contains a chromogenic indicator system and sodium azide resulting in a calorimetric response if ethanol is present. The calorimetric change is transmitted to a color detector through optic fiber. The color detector is a part of electronic circuitry which initiates one or more functions when the color change is detected. The circuit may energize warning indicia such as a lamp. The circuit may also disable a vehicle which is being operated. The operation of the system may be initiated by first testing the pH level in the skin of individual to determine if it is above 6.7. A pH level of greater than 6.7 is known to be an indicator of alcohol consumption.

Referring first to FIG. 1, therein is illustrated an impregnated membrane of a system for inhibiting use of a hand-operated machine by an impaired individual through detection of toxins in the individual according to a preferred embodiment of the invention. The preferred embodiment of the invention is illustrated in the context of a motor vehicle as the "hand-operated machine." The steering wheel of a motor vehicle is a hand-operated portion of a motor vehicle. The system of the preferred embodiment provides a semi-permeable ultra filtration membrane 5 of porous plastic as means for collecting perspiration. The membrane 5 is configured to be received in a steering wheel 20 as illustrated by the slotted steering wheel in FIG. 2. The membrane 5 is thus able to be engaged by the hand 21 of an individual during normal operation of the vehicle through utilization of the steering wheel 20 as illustrated in FIG. 6. Referring now momentarily to FIG. 3, a suitable membrane 5 is a porous plastic having pores designed to cause capillary action increasing its cohesion and chromatography support capabilities and induce flow to the area of least resistance.

Referring again particularly to FIG. 1, the membrane 5 is impregnated with various substances for the operation of the system. For convenience of understanding, these substances are distinctly illustrated in FIG. 1. The membrane 5, or compilation of membranes, contain a sweat inducing substance 1 to be transferred to the skin such as pilocarpine which is a well-known sweat inducing alkaloid. The sweat-inducing substance may also contain substances to block absorption elements by the sweat glands. An element such as the substance to be detected, namely ethanol in the preferred embodiment. These blocking elements may be referred to as buffers and include substances such as glucose-6 phosphate and fructose 6-phosphate. The membrane is also impregnated with an ethanol assay substance 2 to exhibit the presence of ethanol. The substance 2 may contain alcohol oxidase and a paired chromogenic indicator system using DHSA/4 amino tantipyrine and a sodium azide. The membrane 5 can be impregnated at a level of ordinary skill in the art using the known processes of phase inversion to cloud point techniques. Additional substances which may be added to the membrane 5 to enhance its effectiveness are contained in the solutions table below.

Solution 1

Cellulose Acetate (viscosity) 36.0 gm 45) 15% plus 1.5% KP.140 in acetone

15% SMA 26.25A Plus 1–5% 4.0 gm KP in acetone Toluene 2.0 ml

Solution 2

Sorbitol (60%) 1.8 ml

Sodium azide (0.03) 1.8 ml

Emulphor R on 870 (108) 1.0 ml

POD (20mg Id1) 0.5 ml

Add (500 IU/Ml) 1.8 ml 2 propanol 6.0 ml

Phosphate Buffer pH7.5 0.05 m 11.2 ml

A suitable solution for impregnating the membrane 5 is 0.5% gumguaic in chloroform. The solution may be applied by rolling application to the surface of the membrane 5 at speeds of from 10 to 50 feet per minute and then drying the membrane 5 at a flash point of the solvent used. pH detecting capability is added to the system by also impregnating the membrane 5 with a pH assay. The system is thus able to also detect substances having constituents detectable through pH assessment.

Referring now to FIGS. 2 and 4, electrodes 4 and optic fiber are placed in the steering wheel 20. When a current is created through the electrodes 4 iontophoresis is caused to occur in the sweat-inducing substance 1. The electrodes 4 are also used to reset the system or to neutralize the system so that new readings may be taken.

Referring now to FIG. 5, therein is shown in schematic block diagram form an electric circuit 26 for the system. The circuit 26 is designed to automate the sequence of operation of the system. The circuit employs a timing element such as a dual linear timer 7 with supply voltage of +16V. Optical sensors 8 such as x-sunx/RS.52D MSG are used to detect color changes. Electrolite polymer optical fibers 9 (1 mm diameter unjacketed) are suitable for receiving the color change and directing it to the optical sensor 8. A precision miniature halogen lamp 10 such as xenon technology 4000 hrs lamp is suitable for use to provide illumination of the color change to be detected. To determine if the vehicle is experiencing a continuous yaw a gyro switch 11 is employed such as a model known as 360 degrees continuous yaw. Optical Encoder Electronics, motor speed 167 hz, power 13ma. A suitable speed switch 13 is the ultra compact EssD of Synchro Start.

In operation, the electronic circuitry 26 is activated when an individual who has grasped the steering wheel 20 and starts driving the vehicle exhibits a pH level of greater than 6.7 or if the vehicle exhibits yawing without the turn signal being used. The pH of the individual is detected for 30 seconds when the engine of the vehicle is started. If there is no pH level detected but yawing is detected the system responds by illuminating the warning lamp 14. This is an indication for the driver to place the natural surface of his or her hands upon the steering wheel for 30 seconds. If this is not done the unit will begin the automation procedure as if the driver were intoxicated. When the system is activated the ethanol assay substance 2 in the membrane 5 runs a qualitative using the operator's secretion. However, if an adequate amount of perspiration has not been produced by the sweat-inducing agent, iontophoresis is begun through electrode 4 energization. This occurs during a 30-second phase. If ethanol is detected in the sweat a calorimetric response which is transmitted by the fiber 24, 9 and read by the optical sensor 8 activates a warning system component such as vehicle lights, horn, automatic override or speed switch and cut-off. When the ability to operate the vehicle has been terminated by the system (after an automatic takeover) the ignition key of the vehicle must be turned to the on position and then the hands of the operator must remain firmly fixed on the wheel for 60 seconds so that new readings may be taken.

Other modifications may be made in the foregoing without departing from the scope and spirit of the claimed invention. For example,

What is claimed is:

1. An apparatus for inhibiting use of a hand-operated machine by an impaired individual comprising:

means for receiving perspiration from hands of the individual juxtaposed with means for operating the hand-operated machine by hand such that when the means for operating the hand-operated machine by hand is engaged said means for receiving perspiration from the hands of the individual is placed in contact with the hands of the individual;

ethanol assay means disposed in combination with said means for receiving perspiration from the hands of the individual for reacting with ethanol in the perspiration of the individual;

means for causing a mixture of said ethanol assay means and said ethanol to exhibit a color change;

means for detecting said color change and producing an electrical signal in response to said color change; and means for causing said electrical signal to energize circuitry which inhibits operation of the hand-operated machine.

2. The system of claim 1, said means for receiving perspiration from hands of the individual comprising porous plastic.

3. The system of claim 2, further comprising means for inducing perspiration in the individual juxtaposed with said means for receiving perspiration from hands of the individual.

4. The system of claim 3, said means for inducing perspiration in the individual comprising iontophoresis-activated pilocarpine.

5. The system of claim 3, further comprising means for activating said means for inducing perspiration in the individual when either a pH level of greater than 6.7 is detected in the hands of the individual engaging said means for operating the hand-operated machine by hand or the hand-operated machine exhibits a predetermined attitude in motion.

6. The system of claim 5, said means for activating said means for inducing perspiration in the individual when a pH level of greater than 6.7 is detected in the hands of the individual engaging said means for operating the hand-operated machine by hand comprising:

a pH assay juxtaposed with said means for receiving perspiration from hands of the individual; and means for initiating said means for inducing perspiration in the individual when said pH assay produces a response indicating that a pH level of greater than 6.7 has been detected.

7. The system of claim 1, further comprising means for inhibiting absorption of said ethanol by sweat glands of the individual.

8. The system of claim 7, said means for inhibiting absorption of said ethanol by sweat glands of the individual comprising a sugar biologically-absorbable through skin admixed with said iontophoresis-activated pilocarpine.

* * * * *